US009336925B1

(12) United States Patent
Guo et al.

(10) Patent No.: US 9,336,925 B1
(45) Date of Patent: May 10, 2016

(54) SILOXANES, DOPED SILOXANES, METHODS FOR THEIR SYNTHESIS, COMPOSITIONS CONTAINING THE SAME, AND FILMS FORMED THEREFROM

(71) Applicant: Thin Film Electronics ASA, Oslo (NO)

(72) Inventors: Wenzhuo Guo, Cupertino, CA (US); Brent Ridley, Huntington Beach, CA (US); Joerg Rockenberger, San Jose, CA (US)

(73) Assignee: Thin Film Electronics ASA, Oslo (NO)

( * ) Notice: Subject to any disclaimer, the term of this patent is extended or adjusted under 35 U.S.C. 154(b) by 305 days.

(21) Appl. No.: 13/889,149

(22) Filed: May 7, 2013

Related U.S. Application Data

(62) Division of application No. 12/625,492, filed on Nov. 24, 2009, now abandoned.

(60) Provisional application No. 61/118,419, filed on Nov. 26, 2008.

(51) Int. Cl.
| C08G 77/04 | (2006.01) |
| H01B 3/02 | (2006.01) |
| H01L 21/02 | (2006.01) |
| C07F 7/02 | (2006.01) |
| C07F 7/08 | (2006.01) |
| C08G 77/06 | (2006.01) |

(52) U.S. Cl.
CPC .......... *H01B 3/025* (2013.01); *H01L 21/02126* (2013.01); *C07F 7/025* (2013.01); *C07F 7/0834* (2013.01); *C08G 77/04* (2013.01); *C08G 77/06* (2013.01)

(58) Field of Classification Search
None
See application file for complete search history.

(56) References Cited

U.S. PATENT DOCUMENTS 2,810,628 A   10/1957   Bailey et al.
4,310,482 A *  1/1982   Baney .......................... 264/625
(Continued)

FOREIGN PATENT DOCUMENTS

EP   1 087 433 A1   3/2001
JP   6-191821 A     7/1994
JP   2001-308020 A  11/2001

OTHER PUBLICATIONS

Kotaro Yano, Yutaka Kitsuno, Shoichi Tazawa, and Keiji Kawasaki; "Higher Order Silane Containing Solution for Forming Silicon Film"; Patent Abstracts of Japan; Publication No. 06191821 A; Publication Date: Jul. 12, 1994; Japanese Patent Office, Japan.

(Continued)

*Primary Examiner* — Robert S Loewe
(74) *Attorney, Agent, or Firm* — Andrew D. Fortney; Central California IP Group, P.C.

(57) ABSTRACT

In one aspect, the present invention provides undoped and doped siloxanes, germoxanes, and silagermoxanes that are substantially free from carbon and other undesired contaminants. In a second aspect, the present invention provides methods for making such undoped and doped siloxanes, germoxanes, and silagermoxanes. In still another aspect, the present invention provides compositions comprising undoped and/or doped siloxanes, germoxanes, and silagermoxanes and a solvent, and methods for forming undoped and doped dielectric films from such compositions. Undoped and/or doped siloxane compositions as described advantageously provide undoped and/or doped dielectric precursor inks that may be employed in forming substantially carbon-free undoped and/or doped dielectric films.

20 Claims, 6 Drawing Sheets

(56) References Cited

U.S. PATENT DOCUMENTS

| | | | |
|---|---|---|---|
| 5,153,295 A * | 10/1992 | Whitmarsh et al. | 528/31 |
| 5,254,439 A | 10/1993 | Tani et al. | |
| 5,700,400 A * | 12/1997 | Ikai et al. | 252/513 |
| 6,005,036 A * | 12/1999 | Carrozza et al. | 524/265 |
| 6,503,570 B2 * | 1/2003 | Matsuki et al. | 427/387 |
| 6,517,911 B1 * | 2/2003 | Matsuki | 427/551 |
| 6,610,872 B1 * | 8/2003 | Choi et al. | 556/53 |
| 7,052,980 B2 | 5/2006 | Aoki | |
| 7,078,276 B1 * | 7/2006 | Zurcher et al. | 438/151 |
| 2003/0045632 A1 * | 3/2003 | Shiho et al. | 524/861 |
| 2003/0229190 A1 * | 12/2003 | Aoki et al. | 526/279 |
| 2004/0029364 A1 * | 2/2004 | Aoki et al. | 438/478 |
| 2004/0248429 A1 | 12/2004 | Aoki | |
| 2006/0159859 A1 * | 7/2006 | Iwasawa | 427/515 |
| 2013/0026453 A1 * | 1/2013 | Kunze et al. | 257/40 |

OTHER PUBLICATIONS

Yasuo Matsuki and Satoshi Ehata; "Silicon Film and Method of Forming its Pattern"; Patent Abstracts of Japan; Publication No. 2001-308020; Publication Date: Nov. 2, 2001; Japanese Patent Office, Japan.

* cited by examiner

4A

4B

4C

4D

5A

5B

6A

6B

6C

6D

6E

6F

6G

6H

SILOXANES, DOPED SILOXANES, METHODS FOR THEIR SYNTHESIS, COMPOSITIONS CONTAINING THE SAME, AND FILMS FORMED THEREFROM

RELATED APPLICATIONS

This application is a divisional of claims the benefit of U.S. patent application Ser. No. 12/625,492, filed Nov. 24, 2009, pending, which claims the benefit of U.S. Provisional Application No. 61/118,419, filed Nov. 26, 2008, incorporated herein by reference in its entirety

FIELD OF THE INVENTION

The present invention generally relates to the field of doped and undoped siloxane compounds and/or polymers. More specifically, embodiments of the present invention pertain to doped and undoped siloxane compounds and/or polymers, methods for their synthesis, compositions containing such doped and undoped siloxane compounds and/or polymers, and films formed therefrom.

DISCUSSION OF THE BACKGROUND

Conventional spin-on glass (SOG) formulations may be used in the manufacture of dielectric films in semiconductor devices. However, such formulations typically comprise a carbon-containing monomeric precursor. Accordingly, after decomposition of such a SOG formulation, the resultant dielectric film may contain significant amounts of carbon due to incorporation of some of the carbon from the monomer.

SUMMARY OF THE INVENTION

In one aspect, the present invention relates to a siloxane, germoxane, or silagermoxane compound containing at least 3 A atoms, comprising units of the formula —(OA[$O_dH$])—, —(OA[$O_dH$]$_2$)—, —(OA[$O_dH$]$_3$) or -(c-(OA)$_q$[$O_dH$]$_{2q-x}$)—, where each instance of A is independently Si or Ge, each instance of q is independently an integer from 3 to 12, each instance of x is independently an integer from 0 to q, and each instance of d is independently 0 or 1. In a further aspect, the siloxane, germoxane, or silagermoxane further comprises one or more units of the formula $O_cDR^1_p$, where each instance of D is independently Sb, As, P, B or Al, each instance of p is independently an integer from 0 to 2, and each instance of $R^1$ is independently alkyl, aryl, aralkyl, H, OH or $AR^2_3$, where $R^2$ is H, OH or —(OA)$_y$($O_cH$)$_{2y+i}$, where y is an integer from 1 to 4, and each instance of c is independently 0 or 1.

In a second aspect, the present invention relates to a method of making a siloxane, germoxane, or silagermoxane compound, comprising mixing a linear, branched, cyclic or caged silane, germane, or silagermane containing at least three A atoms, comprising units of the formula -(AH)—, -($AH_2$)—, -($AH_3$), -(c-$A_qH_{2q-1}$) and/or -(c-$A_qH_{2q-x}$)—, where each instance of A is independently Si or Ge, each instance of q is independently an integer from 3 to 12, and each instance of x is independently an integer from 0 to q, with a solvent, and reacting the silane, germane, or silagermane compound with an oxygen source that contains substantially no carbon atoms to form the siloxane, germoxane, or silagermoxane. In a further aspect, the linear, branched, cyclic or caged silane, germane, or silagermane of the present method further comprises one or more units of the formula $DR^1_p$, where each instance of D is independently Sb, As, P, B or Al, each instance of p is independently an integer from 0 to 2, and each instance of $R^1$ is independently alkyl, aryl, aralkyl, H, or $AR^2_3$, where $R^2$ is H, or -$A_yH_{2y+i}$, and y is an integer from 1 to 4. The oxygen source may comprise any source of oxygen that does not contain undesired contaminants (e.g., carbon), including air, $H_2O_2$, $O_2$, or $O_3$, although alternative oxidants and/or oxygen sources (e.g., $N_2O$) may also be employed.

In a third aspect, the present invention relates to a composition comprising a siloxane, germoxane, or silagermoxane, and a solvent in which the siloxane, germoxane, or silagermoxane is soluble. In a further aspect, the composition may further comprise one or more dopant compounds of the formula $D_aR^1_b$, where D is Sb, As, P, or Al; a is from 1 to 20; b is from 0 to 26 or an integer corresponding to the number of binding sites available on the a instances of D; each of the b instances of $R^1$ is independently H, alkyl, aryl, aralkyl, a halogen, O, $OR^2$, $NR^2_2$ or $AR^{2'}_3$; where $R^2$ is hydrogen, alkyl, aryl, aralkyl, or a halogen; $R^{2'}$ is hydrogen, alkyl, aryl, aralkyl or $A_yH_{2y+1}$; and y is an integer of from 1 to 4.

In still another aspect, the present invention relates to a method of making a dielectric film, comprising the steps of coating or printing a composition comprising a siloxane, germoxane, or silagermoxane and a solvent in which the siloxane, germoxane, or silagermoxane is soluble on a substrate, and converting the composition to the dielectric film.

These and other advantages of the present invention will become readily apparent from the detailed description of preferred embodiments below.

DETAILED DESCRIPTION

Figure 1:
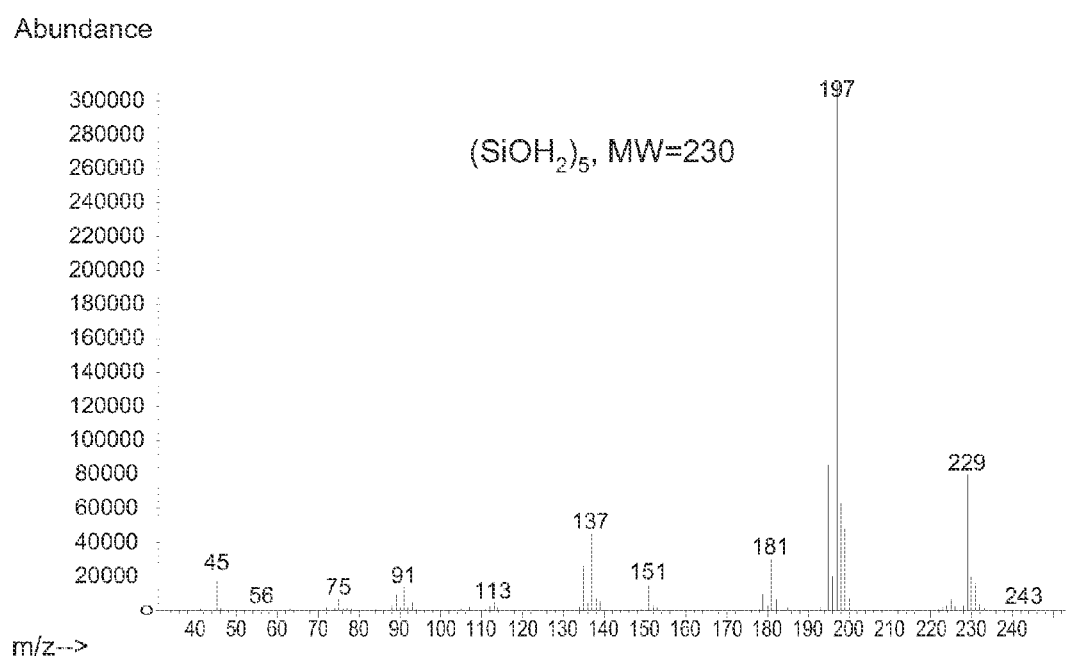
FIG. 1 is a GC-MS spectrum of an exemplary siloxane.

Reference will now be made in detail to the various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description of the present invention, numerous specific details are set forth in order to provide a thorough understanding of the present invention. However, it will be readily apparent to one skilled in the art that the present invention may be practiced without these specific details. In other instances, well-known methods, procedures and components have not been described in detail so as not to unnecessarily obscure aspects of the present invention.

For the sake of convenience and simplicity, the terms "$C_a$-$C_b$ alkyl," "$C_a$-$C_b$ alkoxy," etc., shall refer to both branched and unbranched moieties, to the extent the range from a to b covers 3 or more carbon atoms. Unless otherwise indicated, the terms "arene," "aryl," and "ar-" refer to both mono- and polycyclic aromatic species that may be unsubstituted or substituted with one or more conventional substituents, to the extent possible and/or applicable. The terms "silane," "polysilane" and "(cyclo)silane" may be used interchangeably herein, and unless expressly indicated otherwise, these terms individually refer to a compound or mixture of compounds that consists essentially of (1) silicon and/or germanium and (2) hydrogen. The terms "doped silane," and "doped polysilane" may also be used interchangeably herein, and unless expressly indicated otherwise, these terms individually refer to a compound or mixture of compounds that consists essentially of (1) silicon and/or germanium, (2) hydrogen, and (3) one or more dopant atoms (which may have one or more substituents attached thereto as described elsewhere herein). The prefix "(cyclo)-" generally refers to a compound or mixture of compounds that may contain a cyclic ring, and the prefix "cyclo-" or "c-" generally refers to a compound or mixture of compounds that contain one or more cyclic rings. For the sake of brevity, the terms "halo-," "halide," "halogen" and grammatical derivations thereof may describe halogens as defined in the Periodic Table of Elements (F, Cl, Br, and I) and halogen-like species (e.g., that form stable monovalent anions) such as methanesulfonate (OMs), trifluoromethanesulfonate (OTf), toluenesulfonate (OTs), tetrafluoroborate ($BF_4$), hexafluorophosphate ($PF_6$), etc. Also, the terms "isolating" and "purifying" (and grammatical variations thereof) may be used interchangeably herein, but these terms are intended to have their art-recognized meanings, unless indicated otherwise. Furthermore, for the sake of brevity, the terms "siloxane" and "oxidized silane" may be used interchangeably herein, and unless otherwise specified, generally to refer to linear, branched, cyclic or caged siloxanes, germoxanes, and silagermoxanes consisting essentially of silicon, germanium, hydrogen and/or oxygen. The term "doped siloxane," unless expressly indicated otherwise, refers to a compound or mixture of compounds that consists essentially of (1) silicon and/or germanium, (2) hydrogen, (3) oxygen and (4) one or more dopant atoms (which may one or more have substituents attached thereto as described elsewhere herein). Unless otherwise noted, the terms "ink," "formulation" and "composition" may be used interchangeably herein, and generally refer to compositions comprising a doped or undoped siloxane, germoxane, silagermoxane, or a mixture thereof in a solvent.

Pure cyclopentasilane (>99.9 at. % Si and H) and polysilanes (>99.6 at. % Si and H) can be made by known methods (see, e.g., U.S. Pat. Nos. 7,422,708, 7,553,545, 7,498,015, and 7,485,691, also see U.S. patent application Ser. No. 11/867,587, filed Oct. 4, 2007; and U.S. patent application Ser. No. 11/543,414, filed Oct. 5, 2006, the relevant portions of each of which are incorporated herein by reference). Methods of preparing heterocyclosilanes (see, e.g., U.S. patent application Ser. No. 10/950,373, filed Sep. 24, 2004; U.S. patent application Ser. No. 10/949,013, filed Sep. 24, 2004; and U.S. patent application Ser. No. 10/956,714, filed Oct. 1, 2004; the relevant portions of each of which are incorporated herein by reference) and doped polysilanes (see, U.S. patent application Ser. No. 11/867,587, filed Oct. 4, 2007, the relevant portions of which are incorporated herein by reference) are also known.

In one aspect, the present invention provides methods for making undoped and/or doped siloxanes by introducing oxygen in a controlled manner to a solution of a high-purity undoped and/or doped cyclosilane, polysilane and/or other silane. An undoped and/or doped cyclic siloxane, polysiloxane, and/or other siloxane provides a substantially carbon-free component of a dielectric precursor ink, since the precursor molecules do not contain Si—O—C and/or Si—C bonds. Doped siloxane compounds may contain carbon substituent groups (e.g., tert-butyl, iso-propyl) bound to a dopant atom. However, the lability of the dopant atom—carbon atom bond allows for their removal in a subsequent film-forming process without substantially increasing the carbon content of a film formed from a composition containing such doped siloxane compounds. A substantially carbon free film can be formed by the substantially complete removal of the carbon-containing leaving groups from the substituents on the dopant atom(s), which can usually be accomplished by formation of small volatile molecules during the decomposition process of the doped oxidized silane compounds. Accordingly, the present invention advantageously provides undoped and/or doped dielectric inks that leads to substantially carbon-free undoped and/or doped dielectric films.

Doped siloxanes may also be formed by introducing dopant(s) (e.g., boron, phosphorous, etc.) and/or dopant precursor(s) (e.g., $B_2H_6$ or other hydroboranes, compounds of the formula $PR_3$ or $BR_3$) to a cyclosilane, polysilane and/or other silane, either before or after an oxidation step. For example, doped siloxanes may be formed by adding a dopant and/or dopant precursor (e.g., mono-, di- or tri-tert-butylphosphine or oxidized analogs thereof) to a cyclosilane, polysilane and/or other silane before an oxidation step. Doping of such cyclosilanes and/or polysilanes prior to an oxidation step may incorporate dopant atoms (e.g., via oxidative incorporation of the dopant and/or dopant precursor in the cyclosilane, polysilane and/or other silane) into a resulting doped cyclic siloxane and/or doped polysiloxanes. Alternatively, a doped siloxane ink can be also formed by oxidizing a heterocyclosilane, hetero-substituted (cyclo)silane, heteropolysilane and/or hetero-substituted polysilane. In still another alternative, a doped siloxane composition can be obtained by combining a siloxane and/or doped siloxane with a solvent and one or more dopant compounds.

Such doped and undoped siloxane, germoxane and silagermoxane compounds and compositions enable the formation of doped or undoped silicon oxide films, islands and/or features in electrical devices from liquid phase components by, e.g., spincoating, inkjetting, dropcasting, gravure printing, flexographic printing, spray coating, screen printing, offset printing, spin coating, slit coating, extrusion coating, dip coating, meniscus coating, microspotting, pen-coating, stenciling, stamping, syringe dispensing, pump dispensing, etc., followed by a subsequent curing step (see, e.g., U.S. patent application Ser. No. 11/452,108, filed Jun. 12, 2006; U.S. patent application Ser. No. 11/888,949, filed Aug. 3, 2007; U.S. patent application Ser. No. 11/888,942, filed Aug. 3, 2007; U.S. patent application Ser. No. 11/818,078, filed Jun. 12, 2007; and U.S. patent application Ser. No. 12/109,338, filed Apr. 24, 2008; the relevant portions of each of which are incorporated herein by reference).

The invention, in its various aspects, will be explained in greater detail below with regard to exemplary embodiments.

Exemplary Methods for Making Siloxanes, Germoxanes and Silagermoxanes

In one embodiment, the present invention concerns a method of making a siloxane, germoxane, or silagermoxane compound including mixing a linear, branched, cyclic or caged silane, germane, or silagermane containing at least three A atoms, comprising units of the formula -(AH)—, -($AH_2$)—, -($AH_3$), -(c-$A_qH_{2q-1}$) and/or -(c-$A_qH_{2q-x}$)—, where each instance of A is independently Si or Ge, each instance of q is independently an integer from 3 to 12, and each instance of x is independently an integer from 0 to q, with a solvent, and reacting the silane, germane, or silagermane compound with an oxygen source that contains substantially no carbon atoms to form the siloxane, germoxane, or silagermoxane.

In some embodiments, the linear, branched, cyclic or caged silane, germane, or silagermane may include monomers consisting essentially of silicon and/or germanium and hydrogen. For example, the monomer may comprise a silane compound of the formula $A_nH_{2n+2}$ and/or a cyclosilane compound of the formula $c-A_qH_{2q}$, where each instance of A is independently Si or Ge; n is an integer of from 3 to 20; and q is an integer of from 3 to 12. In various embodiments, A is Si, n is an integer of from 5 to 10, and q is an integer from 4 to 8. In one embodiment, A is Si and q is 5 (i.e., the monomer is cyclopentasilane). Such monomers may be commercially obtained, synthesized by known methods, and/or prepared according to the methods described in U.S. Pat. No. 7,498, 015.

In additional embodiments, the linear, branched, cyclic or caged silane, germane, or silagermane may include an oligosilane and/or polysilane consisting essentially of (i) hydrogen and (ii) silicon and/or germanium, having a molecular weight of from about 180 to about 2300 g/mol (e.g., from about 450 to about 2300 g/mol, or any other range of values therein). Alternatively, the oligosilane or polysilane may have a chain length of from 10 to 10,000, 100,000 or 1,000,000 silicon and/or germanium atoms. Such oligosilanes and/or polysilanes may be prepared as described in U.S. Pat. No. 7,485,691, U.S. patent application Ser. No. 11/867,587, filed Oct. 4, 2007, and U.S. patent application Ser. No. 11/543,414, filed Oct. 5, 2006.

To make a siloxane, germoxane, or silagermoxane, a silane, cyclosilane and/or polysilane is dissolved in a solvent. The silane, cyclosilane and/or polysilane or mixture thereof may be present in the solution in any amount, for example from 1-99 wt % (e.g., 1-40 wt %, or any other range of values therein). The solvent may comprise a hydrocarbon solvent (e.g., a $C_5$-$C_{12}$ alkane, a cycloalkane, a $C_6$-$C_{12}$ arene and an alkylated arene), a $C_5$-$C_{12}$ alcohol (e.g., pentanol, hexanol, cyclohexanol, octanol, decanol, dodecanol), a $C_4$-$C_{12}$ ether alcohol containing from 2 to 4 oxygen atoms (e.g., butyl carbitol, tetrahydrofurfuryl alcohol, and dipropylene glycol butyl ether), a polyether, a methicone, an amide of a $C_1$-$C_4$ alkanoic acid containing up to 2 $C_1$-$C_4$ alkyl groups (e.g., formamide, dimethyl formamide), a $C_2$-$C_4$ sulfoxide (e.g., dimethyl sulfoxide), and a cyclic ester or diester of a $C_2$-$C_{10}$ hydroxylated alkanoic acid (e.g., butyrolactone). In addition, the solvent may be selected from, e.g., $C_1$-$C_4$ alcohols (methanol, ethanol, propanol, isopropanol, butanol), $C_1$-$C_4$ alkyl esters of $C_1$-$C_4$ alkanoic acids (ethyl acetate), $C_4$-$C_8$ ethers (diethyl ether, dibutyl ether, methyl t-butyl ether, tetrahydrofuran), $C_3$-$C_6$ ketones (acetone, methyl ethyl ketone, methyl t-butyl ketone, cyclopentanone, cyclohexanone), siloxanes (e.g., cyclo-$([Me_2Si]O)_3$, cyclo-$([Me_2Si]O)_4$, etc.), and mixtures thereof. However, the solvent is not particularly limited, and may be essentially any solvent that does not interfere with or adversely affect the oxidation reaction, or introduce undesired contaminants into a product siloxane mixture.

An oxygen source and/or oxidizing agent is then introduced into the solution to effect a reaction between the silane, cyclosilane and/or polysilane or mixture thereof and the oxygen source. The oxygen source and/or oxidizing agent may comprise any source of oxygen that does not contain undesired contaminants. A wide variety of oxygen sources and/or oxidizing agents may be employed, such as air or $H_2O_2$. In preferred embodiments, the oxygen source is $O_2$, $O_3$ or $H_2O_2$.

Alternative oxidants and/or oxygen sources may also include gaseous oxygen sources (e.g., $N_2O$), alkali and/or alkaline earth metal-based oxidants (e.g., peroxides such as $NaO_2H$ and/or bases such as LiOH), transition metal-based oxidants (e.g., ruthenium tetroxide, osmium tetroxide, etc.), and actinide and/or lanthanide metal-based oxidants (e.g. oxocomplexes and peroxides), which may be used alone or in combination with other oxygen sources and/or oxidizing agents.

When in the gas phase, the oxygen source and/or oxidant may be introduced into the reaction mixture by a gas bubbler, syringe, or by vigorous stirring in an atmosphere containing the oxygen source and/or oxidant. A gas phase oxygen source may also contain an inert component such as $N_2$, Ar, He, etc., and such mixtures may be dried by passing through or over a desiccant (such as anhydrous $CaCl_2$, $CaSO_4$, $BaSO_4$, $P_2O_5$, etc.) before introduction into the reaction mixture. Liquid phase oxygen sources and/or oxidants or solutions of solid phase oxygen sources and/or oxidants may be added, for example, via syringe or dropping funnel, either in a single aliquot or over a period of time (e.g., 1 minute to 24 hours, 10 minutes to 12 hours, or any value therein). Solid oxygen sources and/or oxidants may be added in a single portion (by, e.g., a solid addition funnel), or may be added in several portions over a period of time (e.g., 1 minute to 24 hours, 10 minutes to 12 hours, or any value therein) by, e.g., a metering solid addition funnel or apparatus.

Figure 2:
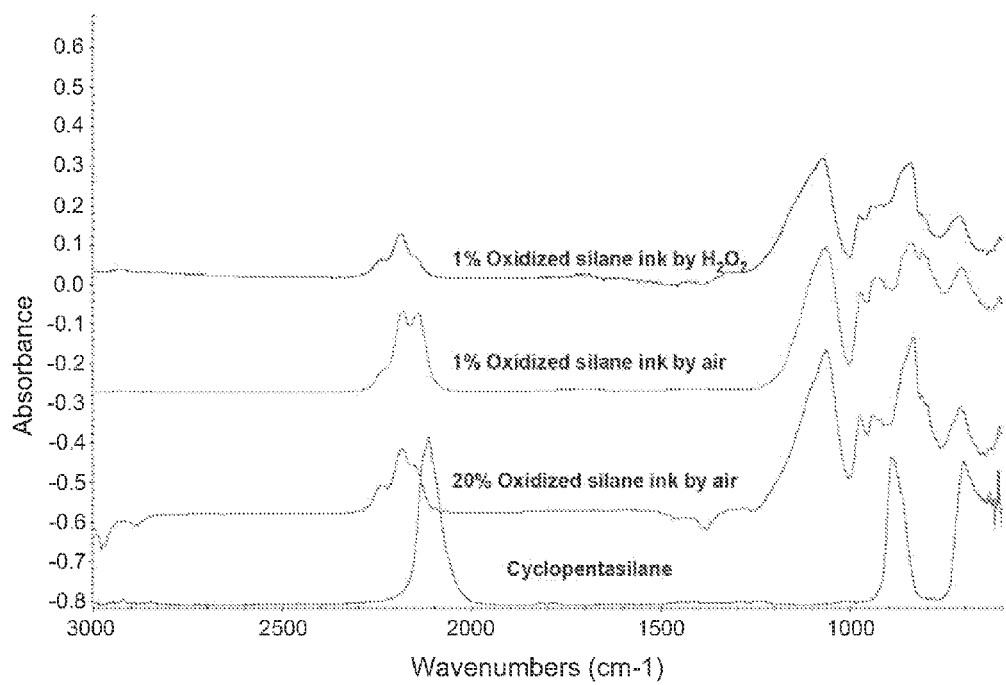
FIG. 2 is a series of overlaid FT-IR spectra showing the spectral characteristics of various exemplary siloxanes.

The reaction may be conducted at any temperature at which the reaction occurs (e.g., a temperature of from −78° C. to 400° C., or any value or range of values therein), but the reaction generally appears to proceed smoothly at room temperature or ambient temperature (e.g., from about 15° C. to about 30° C.). The reaction may be monitored by spectroscopy (e.g., FT-IR spectroscopy, $^1$H, $^{17}$O, or $^{29}$Si NMR spectroscopy), thin-layer chromatography, mass spectrometry, or any other known technique for monitoring the extent of the oxidation reaction. The reaction may be conducted for a length of time sufficient to effect a desired degree of oxidation of the silane, cyclosilane and/or polysilane or mixture thereof. For example, as shown in FIG. 1, the extent of oxidation of cyclopentasilane was determined by analyzing an aliquot of the reaction mixture by GC-MS. A peak corresponding to $(SiOH_2)_5$ was observed at m/z=230, indicating the presence of cyclopentasiloxane (or a constitutional isomer thereof). Similarly, as shown in FIG. 2, FT-IR spectra of cyclopentasiloxane compositions are overlaid, showing similar absorptions amongst solutions containing various weight percentages of cyclopentasiloxane relative to a cyclopentasilane solution. FIG. 2 also shows spectral characteristics of cyclopentasiloxane prepared with air (middle two spectral traces) vs. cyclopentasiloxane prepared with $H_2O_2$ (top spectral trace).

Figure 3:
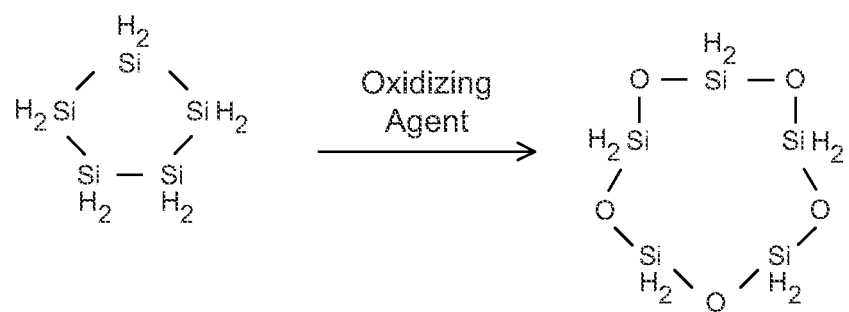
FIG. 3 is a diagram showing an exemplary embodiment of the present method.

The reaction may be stopped by ceasing addition of the oxygen source and/or oxidizing agent, and/or by purging the solution with an inert gas such as Ar, $N_2$, etc. In the case of oxygen sources and/or oxidizing agents that are not substantially soluble in the solution (e.g., sparingly soluble or insoluble solids), filtration may be used to remove the oxygen source and stop the reaction. Alternatively, in the case where an oxygen source is a soluble liquid, the reaction may be stopped, for example, by adding scavenging agent (e.g., a compound that will preferentially react with the oxygen source in the reaction mixture) or by differential extraction (e.g., extraction with a solvent in which the siloxane and the oxygen source exhibit differing solubility). The reaction may be stopped when, for example, all Si—Si bonds are broken to form —Si—O—Si— bonds, as shown in FIG. 3. Furthermore, an oxygen source and/or oxidizing agent may be selected according to its relative reactivity toward Si—Si bonds and Si—H bonds. Careful selection of the oxygen source and/or oxidizing agent may enable selective oxidation at desired atoms and/or bonds (e.g., Si—Si bonds) while leaving other atoms and/or bonds (e.g., Si—H bonds) unoxidized. Alternatively, the reaction may be conducted for sufficient time or with a sufficiently reactive oxygen source and/or oxidizing agent to oxidize some or all Si—H bonds to form Si—O—H units.

The oxidation reaction may be conducted for a length of time sufficient to oxidize an undoped silane, germane, or silagermane to a desired degree. A higher degree of oxidation in the product siloxane may result in a concomitant increase in the viscosity of a solution of the siloxane. Accordingly, the oxidation reaction may be conducted to provide a desired degree of oxidation that corresponds to a desired viscosity. Furthermore, an appropriate oxygen source and/or oxidizing agent can be selected to provide a desired or targeted degree of oxidation (e.g., having a specific reactivity toward certain bonds in a starting silane), thus enabling "tuning" of the rheology of the resultant siloxane ink as a function of the degree of oxidation of the siloxane in the ink.

A product siloxane, germoxane or silagermoxane solution may be used directly without further treatment and/or purification, e.g., in the case where a gaseous oxygen source is used, and the solution contains substantially no undesired byproducts in the product solution. Alternatively, where removal of an oxygen source and/or oxidizing agent and/or byproducts associated with an oxidation reaction and/or neutralization of an oxidizing agent, or purification of the product is desired, the product may be isolated prior to further use. In addition, unreacted silane starting material may be present in the product mixture, and may be removed if desired. The siloxane, germoxane or silagermoxane may be isolated by standard purification processes (e.g., chromatography, distillation, filtration, extraction) or any other suitable separation technique that does not degrade the siloxane, germoxane or silagermoxane.

Exemplary Methods for Making Doped Siloxanes, Germoxanes and Silagermoxanes

In some embodiments, the linear, branched, cyclic or caged silane, germane, or silagermane may comprise a doped silane, germane, or silagermane. Such a doped silane, germane, or silagermane may comprise a polysilane having one or more units of the formula of the formula $DR^1_p$, where each instance of D is independently Sb, As, P, B or Al, each instance of p is independently an integer from 0 to 2, and each instance of $R^1$ is independently alkyl, aryl, aralkyl, H, or $AR^2_3$, where $R^2$ is H, or $-A_yH_{2y+i}$, and y is an integer from 1 to 4. Doped polysilanes as described may be made according to the methods described in U.S. patent application Ser. No. 11/867,587, filed Oct. 4, 2007, the relevant portions of which are incorporated herein by reference.

In another embodiment, the doped linear, branched, cyclic or caged silane, germane, or silagermane comprises a heterocyclosilane compound of the formula $(AH_z)_g(DR^1)_m$, where g is from 2 to 12, m is 1 or 2, each of the g instances of A is independently Si or Ge, each of the g instances of z is independently 1 or 2, each of the m instances of D is Sb, As, P, B or Al, and each of the m instances of $R^1$ is alkyl, aryl, aralkyl, or $AR^2_3$, where $R^2$ is hydrogen, alkyl, aryl, aralkyl, or $A_yH_{2y+1}$ (where y is an integer of 1 to 4). In various embodiments, A is Si, z is 2, g is (predominantly) 4, and/or m is 1. $R^1$ may be $C_1$-$C_6$ alkyl (e.g., methyl, ethyl, propyl, isopropyl, n-butyl, t-butyl, t-hexyl or t-hexyl[3',3'-dimethylbutyl]), $C_6$-$C_{12}$ aryl (e.g., phenyl, α- or β-naphthyl, tolyl [o-, m- or p-methylphenyl], xylyl [e.g., 1,4-dimethylphenyl], cymyl [o-, m- or p-methylisopropylphenyl], t-butylphenyl, etc.), $C_7$-$C_{12}$ aralkyl (e.g., benzyl, 1,5-dimethylbenzyl, α,α-dimethylbenzyl, etc.), $SiH_3$, or $Si(SiH_3)_3$ (i.e., y=1), although when $R^1$ is $AR^2_3$, $R^2$ can be hydrogen, $C_1$-$C_6$ alkyl, $C_6$-$C_{12}$ aryl or $C_7$-$C_{12}$ aralkyl as described above. In certain implementations, $R^1$ is t-butyl or phenyl.

In some embodiments, undoped and doped silanes as previously described herein may be combined to form a mixture, then the mixture may be oxidized to form a doped siloxane. The undoped and doped silanes may be combined in relative amounts to effect a desired dopant concentration in the mixture, a corresponding dopant atom concentration in a product doped siloxane, germoxane, or silagermoxane, a resultant dopant atom concentration in composition formed from such a doped siloxane (taking into account addition of other components of the composition [e.g., a solvent]), and thus, a dopant atom concentration (e.g., atom percent or mol percent) in a doped dielectric film formed therefrom. Relative amounts of each of undoped and doped silanes may be selected in terms of wt %, mol %, or combined on the basis of dopant at % relative to silicon and/or germanium atoms (and each of at %, mol % and wt % may easily be converted to the others by simple calculations employing the atomic masses [as reported in the Periodic Table of the Elements] of the component atoms of interest [e.g., Si, Ge, P, B, Al, etc.] in the mixture). The amount of undoped silane in the mixture may range, for example, from 0.01 mol % or wt % to 99.99 mol % or wt % (e.g., 0.1 mol % or wt % to 50 mol % or wt %, 1 mol % or wt % to 30 mol % or wt % or any value or range of values therein). The amount of doped silane in the mixture may range, for example, from 0.0001 mol % or wt % to 50 mol % or wt % (e.g., 0.001 mol % or wt % to 30 mol % or wt %, 0.01 mol % or wt % to 10 mol % or wt %, 0.1 mol % or wt % to 10 mol % or wt %, or any value or range of values therein).

In another embodiment, a silane (e.g., a doped and/or undoped silane) and one or more dopant compounds may be combined prior to an oxidation reaction. The one or more dopant compounds have the formula $D_aR^1_b$, where D is Sb, As, P or B or Al; a is from 1 to 20; b is from 0 to 26 or an integer corresponding to the number of binding sites available on the a instances of D; each of the b instances of $R^1$ is independently H, alkyl, aryl, aralkyl, a halogen, O, $OR^2$, $NR^2_2$ or $AR^{2'}_3$; where $R^2$ is hydrogen, alkyl, aryl, aralkyl, F, Cl, Br, or I; $R^{2'}$ is hydrogen, alkyl, aryl, aralkyl or $A_yH_{2y+1}$; and y is an integer of from 1 to 4. For example, the dopant compound(s) may include one or more soluble organoboranes, (organo)azaboranes, and/or organoborates; boron oxides (e.g., $B_2O_3$), $BX_3$ (where X is a halogen, such as Cl, Br, or I; preferably Cl or Br); an adduct and/or salt of $BF_3$ (e.g., $Et_2O.BF_3$, $NH_4BF_4$, etc.); white or red phosphorous; a phosphorous oxide ($P_2O_5$, $P_4O_{10}$, polyphosphoric acid); one or more organophosphines, -phosphine oxides, -phosphites, and/or -phosphates (preferably organic [e.g., alkyl and/or aryl]phosphate esters); one or more meta- and/or polyphosphates, one or more organophosphazenes and/or -oxophosphazenes; $PX_3$, $PX_5$, and/or $POX_3$; $P(NR_2)_3$, $O=P(NR_2)_3$, and/or $P(=NR)X_3$; and/or Sb and/or As analogs of such phosphorous compounds, such as arsenic oxide(s) and antimony oxide(s) (e.g., $As_2O_3$, $As_2O_5$, $Sb_2O_3$, $Sb_2O_5$).

The one or more dopant compounds may be oxidatively incorporated into a product doped siloxane, and may be added in a desired quantity to provide an overall dopant concentration in the product doped siloxane. As described above with respect to mixtures of undoped and doped silanes, added dopant compound(s) may be present in an amount to effect a desired dopant atom concentration (e.g., atom percent or mol percent) in a doped dielectric film formed from a doped siloxane product. The amount of added dopant may be selected in terms of wt %, mol %, or on the basis of dopant at % relative to silicon and/or germanium atoms in the ink composition. Each of the at %, mol % and/or wt % can be converted to the others by simple calculations employing the atomic masses as reported in the Periodic Table of the Elements of the component atoms of interest [e.g., Si, Ge, P, B, Al etc.] or molecular weights of components in the mixture. The amount of dopant compound(s) in the mixture may be, for example, from 0.0001 mol % or wt % to 50 mol % or wt % (e.g., 0.001 mol % or wt % to 30 mol % or wt %, 0.01 mol % or wt % to 10 mol % or wt %, or any value or range of values therein). The at % of dopant atoms in the composition may be from 0.0001 at % to 40 at % (e.g., 0.001 at % to 20 at %, or any other value or range of values therein) with respect to silicon and/or germanium atoms in the composition.

To make a doped siloxane, germoxane, or silagermoxane, a doped silane, cyclosilane and/or polysilane or an undoped silane and one or more dopant compounds are dissolved in a solvent. The doped silane, cyclosilane and/or polysilane or an undoped silane and one or more dopant compounds may be present in the solution in any amount, for example from 1-99 wt % (e.g., 1-40 wt %, or any other value or range of values therein). The solvent may comprise those solvents and/or mixtures thereof that are suitable for oxidation of undoped silanes as described herein. The solvent is not particularly limited, and may be essentially any solvent that does not interfere with or adversely affect the oxidation reaction, or introduce undesired contaminants into a product doped siloxane mixture.

An oxygen source and/or oxidizing agent is then introduced into the solution to effect a reaction between the doped silane, cyclosilane and/or polysilane or mixture thereof and added dopant (when present) and the oxygen source. The oxygen source and/or oxidizing agent may comprise those oxygen sources and/or oxidizing agents that are suitable for oxidation of undoped silanes as described herein, and may be used alone or in combination with other oxygen sources and/or oxidizing agents. Similarly, the oxygen source and/or oxidant may be introduced by the methods described herein that are suitable for oxidation of undoped silanes.

As described above, the reaction may be conducted at any temperature at which the reaction occurs (e.g., a temperature of from −78° C. to 400° C., or any value or range of values therein), but the reaction generally appears to proceed smoothly at room temperature or ambient temperature (e.g., from about 15° C. to about 30° C.). The reaction may be monitored by spectroscopy (e.g., FT-IR spectroscopy, $^1$H, $^{11}$B (when present), $^{17}$O, $^{29}$Si or $^{31}$P (when present) NMR spectroscopy), thin-layer chromatography, mass spectrometry, or any other known technique for monitoring the extent of the oxidation reaction. The reaction may be conducted for a length of time sufficient to effect a desired degree of oxidation of the doped silane, cyclosilane and/or polysilane or mixture thereof, a mixture of undoped and doped silanes, or a mixture of undoped silane and added dopant. The reaction may be stopped by those methods described herein for the oxidation of undoped silanes. The reaction may be stopped when, for example, essentially all Si—Si bonds are converted to —Si—O—Si— units.

The oxidation reaction may be conducted for a length of time sufficient to oxidize the doped silane, cyclosilane and/or polysilane or mixture thereof, the mixture of undoped and doped silanes, or the mixture of undoped silane and added dopant. A higher degree of oxidation in the product doped siloxane, germoxane, silagermoxane, or mixture thereof and added dopant (when present) may result in a concomitant increase in the viscosity of a solution of the doped siloxane. Accordingly, the oxidation reaction may be conducted to effect a desired degree of oxidation that corresponds to a desired viscosity of a solution containing the doped oxidized silane. Furthermore, an appropriate oxygen source and/or oxidizing agent can be selected to provide a desired or targeted degree of oxidation (e.g., having a specific reactivity toward certain bonds in a starting silane), thus "tuning" of the rheology of the resultant doped siloxane ink.

A product doped siloxane, germoxane or silagermoxane solution may be used directly without further treatment and/or purification, e.g., in the case where a gaseous oxygen source is used, and the solution contains substantially no undesired byproducts in the product solution. Alternatively, where removal of an oxygen source and/or oxidizing agent and/or byproducts associated with an oxidation reaction and/or neutralization of an oxidizing agent, or purification of the product is desired, the product may be isolated prior to further use. In addition, unreacted undoped and/or doped silane starting material and/or added dopant may be present in the product mixture, and may be removed if desired. The product doped siloxane, germoxane or silagermoxane (and unoxidized and/or oxidized added dopant when present) may be isolated by standard purification processes (e.g., chromatography, distillation, filtration, extraction) or any other suitable separation technique that does not degrade the product doped siloxane, germoxane or silagermoxane (and unoxidized and/or oxidized added dopant when present).

Exemplary Siloxanes, Germoxanes and Silagermoxanes

In another aspect, the present invention provides a siloxane, germoxane, or silagermoxane compound containing at least 3 A atoms, comprising units of the formula —(OA[$O_d$H])—, —(OA[$O_d$H]$_2$)—, —(OA[$O_d$H]$_3$) or -(c-(OA)$_q$[$O_d$H]$_{2q-x}$)—, where each instance of A is independently Si or Ge, each instance of q is independently an integer from 3 to 12, each instance of x is independently an integer from 0 to q, and each instance of d is independently 0 or 1. The siloxane, germoxane, or silagermoxane compound may be linear, branched, cyclic or caged. The compound generally comprises (i) hydrogen, (ii) silicon and/or germanium, and (iii) oxygen, and may have from 3 to 10, 10,000, 100,000 or 1,000,000 silicon and/or germanium atoms. The degree of oxidation may be selected according to the oxidation reaction conditions and/or variables described herein in the oxidation of a silane, polysilane and/or cyclosilane. Thus, the product may have a degree of oxidation in terms of an A atom to O atom ratio of from 100:1 to 1:3. In many embodiments, all A atoms are Si. In certain of these embodiments, the siloxane is cyclic, and q is an integer from 4 to 8, and the ratio of Si to O atoms is 1:1. In one embodiment, as shown in FIG. 3, the product is cyclopentasiloxane (i.e., A is Si, q is 5 and d=0).

Figure 4:
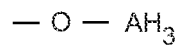
FIG. 4 shows exemplary siloxane structural units.
Figure 4:
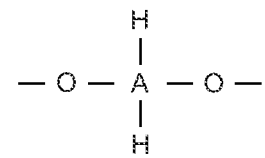
Figure 4:
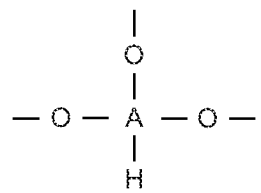
Figure 4:
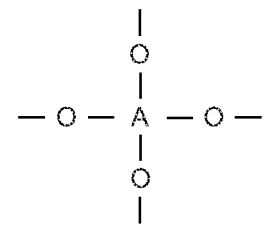

When the product contains both silicon and germanium, the ratio of silicon to germanium atoms is generally the same as the ratio of silicon and germanium atoms present in the starting silane, germane, silagermane or mixture thereof. The relative position of Si and Ge atoms in the chain generally corresponds to the relative position of the Si and Ge atoms in the starting silanes, germanes, silagermanes or mixtures thereof, but may have oxygen atoms incorporated in the chain between the Si and Ge atoms. For example, a monomer chain sequence of —Si—Ge—Ge—Ge—Si—Ge— may be preserved in the product silagermoxane as —Si—O—Ge—O—Ge—O—Ge—O—Si—O—Ge—. In some embodiments, O atoms are incorporated only in Si—Si, Si—Ge and Ge—Ge bonds (e.g., to form Si—O—Si, Si—O—Ge or Ge—O—Ge units), and are not incorporated in Si—H or Ge—H bonds. In other embodiments, Si—H or Ge—H bonds may also be oxidized (e.g., to form Si—O—H or Ge—O—H units). In certain embodiments, as shown in FIG. 4, the siloxane comprises —O-(AH$_3$) (e.g., structure 4A), —O-(AH$_2$)—O— (e.g., structure 4B), —O—(—O-(AH))—O— (e.g., structure 4C) or —O—(—O-A-O—)—O— (e.g., structure 4D) units. In many embodiments, all A atoms are Si.

Figure 5:
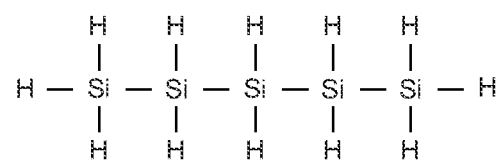
FIG. 5 shows an exemplary siloxane.
Figure 5:
Figure 5:
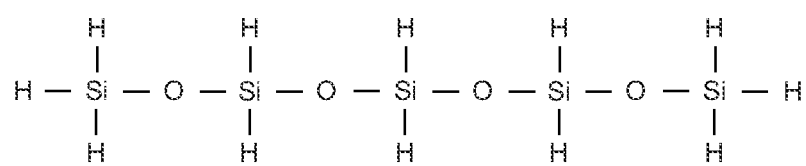

A siloxane, germoxane, or silagermoxane may be formed from small, low molecular weight silanes having a chain length (i.e., a consecutively bonded, continuous chain of Si and/or Ge atoms) from 3 to 10 atoms. The silane starting material (and thus, the siloxane, germoxane, or silagermoxane product) may be cyclic, linear, or branched, and may contain cyclic and acyclic units. For example, as shown in FIG. 5, pentasilane (compound 5A) may be selected as a linear, low molecular weight starting silane. Pentasilane may be oxidized to a range of degrees and/or patterns of oxidation. For example, pentasilane may be oxidized until all —Si—Si— bonds are converted to —Si—O—Si— units (e.g., as shown in compound 5B).

A siloxane, germoxane, or silagermoxane may also be formed from a silane polymer and/or oligomer having a chain length (i.e., a consecutively bonded, continuous chain of Si and/or Ge atoms) of from 10 to 10,000, 100,000 or 1,000,000 silicon and/or germanium atoms. The silane polymer and/or oligomer starting material (and thus, the siloxane, germoxane, or silagermoxane polymer and/or oligomer product) may be cyclic, linear, or branched, and may contain cyclic and acyclic units. A silane polymer may be oxidized, for example, until all —Si—Si-bonds are converted to —Si—O—Si— units.

Exemplary Doped Siloxanes, Germoxanes and Silagermoxanes

In some embodiments, the siloxane, germoxane, or silagermoxane described above further comprises one or more dopant units of the formula $O_cDR^1_p$, where each instance of D is independently Sb, As, P or B, each instance of p is independently an integer from 0 to 2, and each instance of $R^1$ is independently alkyl, aryl, aralkyl, H, OH or $AR^2_3$, where $R^2$ is H, OH or —(OA)$_y$(O$_d$H)$_{2y+i}$, where y is an integer from 1 to 4, and each instance of c is independently 0 or 1. The doped siloxane, germoxane, or silagermoxane compound may be linear, branched, cyclic or caged. The number of dopant atoms present in a product doped siloxane, germoxane, or silagermoxane generally corresponds to the number of dopant atoms present in the doped silane, germane, or silagermane starting material. The compound generally comprises (i) hydrogen, (ii) silicon and/or germanium, (iii) oxygen, and (iv) one or more dopants, and may have from 3 to 10, 10,000, 100,000 or 1,000,000 silicon and/or germanium atoms. In certain embodiments, D is B and c is 0. In other embodiments, D is P and c is 1. A dopant may be present in a doped siloxane in an amount as described above with regard to exemplary methods for making doped siloxanes, germoxanes and silagermoxanes.

When the product contains both silicon and germanium, the ratio of silicon to germanium atoms is generally the same as the ratio of silicon and germanium atoms present in the starting silane, germane, silagermane or mixture thereof. The relative position of Si, Ge and/or dopant atoms in the chain may generally correspond to the relative position of the Si, Ge and/or dopant atoms in the starting doped silane, germane, silagermane or mixtures thereof, mixture of undoped and doped silanes, or mixture of undoped silane and added dopant(s), but may have oxygen atoms incorporated in the chain between the Si, Ge and/or dopant(s) atoms.

Figure 6:
FIG. 6 show exemplary doped siloxane structural units.
Figure 6:
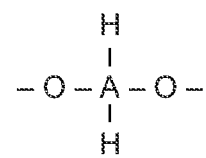
Figure 6:
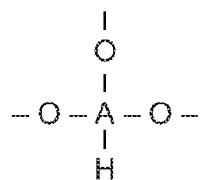
Figure 6:
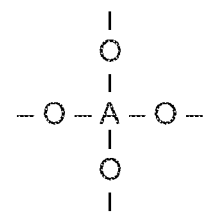
Figure 6:
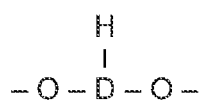
Figure 6:
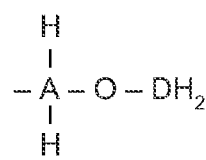
Figure 6:
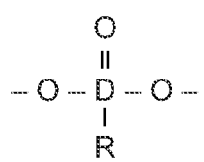
Figure 6:
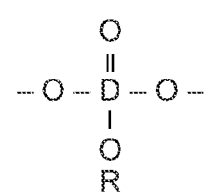

For example, a monomer chain sequence of —Si-D-Ge-D-Si— Ge-D-Si— may be preserved in the product doped silagermoxane as —Si—O-D-O—Ge—O-D-O—Si—O—Ge—O-D-O—Si—. In some embodiments, O atoms may be incorporated only in Si—Si, Si-D, Si—Ge, Ge—Ge, and Ge-D bonds (e.g., to form Si—O—Si, Si—O-D, Si—O—Ge, Ge—O—Ge, or Ge—O-D units), and may not be incorporated in Si—H or Ge—H bonds. In other embodiments, Si—H, Ge—H, or D-H bonds may also be oxidized (e.g., to form Si—O—H, Ge—O—H, or D-O—H units). When R-groups as described above are present on dopants atoms, D-R bonds may also be oxidized to form D-O—R. Thus, as shown in FIG. 6, in certain embodiments, the doped siloxane may contain, for example, —O-(AH$_3$) (e.g., structure 6A), —O-(AH$_2$)—O— (e.g., structure 6B), —O—(—O-(AH))—O— (e.g., structure 6C), —O—(—O-A-O—)—O— (e.g., structure 6D), —O-(DH)—O— (e.g., structure 6E) or -A-O-(DH$_2$) (e.g., structure 6F) units. Furthermore, when D may be susceptible to oxidation (e.g., P, As, Sb), the doped siloxane may contain, for example, O—(R(DO))—O (e.g., structure 6G) or O-(DO(OR))—O (e.g., structure 6H) units may also be present. The structural units shown in FIG. 6 are exemplary, and other structural units may be present in a doped siloxane as will be appreciated by those skilled in the art.

Dopant atoms may or may not be oxidized in a product doped siloxane, germoxane, or silagermoxane, depending on the identity of the dopant atom, the substituent group appended to the dopant atom, and the degree of oxidation effected during the oxidation of a starting doped silane, germane, or silagermane, or a mixture of undoped silane and added dopant. Thus, in the case where dopant atoms are present but remain unoxidized, a similar range of oxidation ratios (Si to O atom ratios) may be effected. However, where dopant atoms are oxidized, the overall ratio of Si to O atoms may be lower than 1:3 (e.g., 1:3.1, 1:3.5, etc.).

A doped siloxane, germoxane, or silagermoxane may be formed from a small, relatively low molecular weight heterosilane having a chain length (i.e., a consecutively bonded, continuous chain of Si and/or Ge and/or dopant atoms) of from 3 to 10 atoms. The heterosilane starting material (and thus, the doped siloxane, germoxane, or silagermoxane) may be cyclic, linear or branched, and may contain cyclic and acyclic units. A heterosilane may be oxidized to a range of degrees and/or patterns of oxidation, as previously described herein.

A doped siloxane, germoxane, or silagermoxane may also be formed from a doped silane polymer and/or oligomer having a chain length (i.e., a consecutively bonded, continuous chain of Si and/or Ge and/or dopant atoms) of from 10 to 10,000, 100,000 or 1,000,000 silicon and/or germanium and/or dopant atoms. The doped silane polymer and/or oligomer starting material (and thus, the doped siloxane, germoxane, or silagermoxane polymer and/or oligomer product) may be cyclic, linear, or branched, and may contain cyclic and acyclic units. For example, as shown in FIG. 10 shows a segment of a doped silane polymer 10 (represented by polymer segment 10A) comprising a branched structure and having greater than 10 Si and dopant units in the longest continuous chain of the polymer, and containing phosphorous dopant atoms substituted with hydrogen. The remaining polymer structure (i.e., other than polymer segment 10A) has been omitted for brevity. The polymer may be oxidized to a range of degrees and/or patterns of oxidation.

Exemplary Siloxane, Germoxane and/or Silagermoxane Compositions

In a further aspect, the present invention relates to compositions comprising one or more siloxanes, germoxanes, silagermoxanes, or mixtures thereof as described herein. The present compositions further comprise a solvent in which the undoped siloxanes, germoxanes, or silagermoxanes are soluble. The siloxane, germoxane, silagermoxane or mixture thereof may be present in the composition in an amount of from 1 to 99 wt % (e.g., from 1 to 40 wt %, from 1 to 20 wt %, or any other range of values therein) of the composition.

The solvents in the present composition are generally those that are liquid at ambient temperatures (e.g., 15-30° C.). The solvent may provide stability and/or an advantageous viscosity and/or volatility to the composition. For example, a solvent or solvent mixture can prevent nozzle clogging in inkjet printing applications and allow the printed composition to dry at relatively low temperatures and relatively short times. Furthermore, the solvent or solvent mixture is generally easily and/or thoroughly removable from the composition. For example, the solvent preferably is one that is substantially completely removed by printing the ink onto a substrate at a temperature of 30-90° C., followed by heating the substrate with the ink printed thereon for e.g., 10 seconds to 12 hours, 1 minute to 1 hour (or any other range of values therein) at a temperature of, e.g., about 30° C. to 200° C., 30° C. to 90° C. (or any other range of values therein).

In various embodiments, the solvent comprises one or more hydrocarbon solvents, such as an alkane, a monocycloalkane, a bicycloalkane, a substituted monocycloalkane, a substituted bicycloalkane, a (cyclic) siloxane and/or a fluoroalkane. Thus, the solvent may be selected from the group consisting of $C_5$-$C_{12}$ linear and/or branched alkanes; $C_6$-$C_{12}$ monocycloalkanes; $C_3$-$C_8$ monocycloalkanes substituted with from 1 to 2n $C_1$-$C_4$ alkyl or halogen substituents or from 1 to n $C_1$-$C_4$ alkoxy substituents, where n is the number of carbon atoms in the monocycloalkane ring; siloxanes of the formula $(R_3Si)(OSiR_2)_p(OSiR_3)$ and cyclosiloxanes of the formula $(SiR'_2O)_q$, where p is from 0 to 4, q is from 2 to 6 (preferably from 3 to 5), each R and R' is independently H, $C_1$-$C_6$ alkyl, benzyl or phenyl substituted with from 0 to 3 $C_1$-$C_4$ alkyl groups (preferably R' is methyl); and $C_3$-$C_8$ fluoroalkanes substituted with from 1 to (2m+2) fluorine atoms and that are liquid at ambient temperatures, where m is the number of carbon atoms in the fluoroalkane. Other apolar and/or non-polar solvents (e.g., saturated hydrocarbons such as $C_5$-$C_{12}$ alkanes, aliphatic ethers such as di-$C_2$-$C_6$ alkyl ethers, methyl $C_4$-$C_6$ alkyl ethers and di-$C_1$-$C_4$ alkyl $C_2$-$C_6$ alkylene diethers [e.g., glyme], cyclic ethers such as tetrahydrofuran and dioxane, arenes such as benzene, toluene and xylenes, etc.) may be included in the present composition.

The composition may also comprise one or more conventional additives, such as a surface tension reducing agent, a surfactant, a binding agent, a thickening agent, a photosensitizer, etc. Preferably, however, the composition is free from components that may introduce undesired impurities into a dielectric film formed from the composition (e.g., carbon, nitrogen, alkali metals, etc.). When they are present, typical amounts of these additives in the composition may be present from 0.01 wt. % to 10 wt. % (e.g., in trace amounts, or from 0.1 wt. % to 5 wt. %) of the composition. A surface tension reducing agent may be present in an amount of from 0.01 wt. % to 1 wt. %, preferably 0.02 wt. % to 0.1 wt. % of the composition. In certain embodiments, the surface tension reducing agent may comprise a conventional hydrocarbon surfactant, a conventional fluorocarbon surfactant or a mixture thereof. A wetting agent may be present in an amount of from 0.05 wt. % to 1 wt. %, preferably 0.1 wt. % to 0.5 wt. % of the ink composition. A surfactant may be present in an amount of from 0.01 wt. % to 1 wt. %, preferably 0.05 wt. % to 0.5 wt. % of the ink composition. A binder and/or thickening agent may be present in an amount sufficient to provide the composition with predetermined flow properties at a given processing temperature. However, it should be noted that such additives are not necessary. In fact, it may be advantageous to exclude the additives from the composition, particularly where such additional components include sufficiently high molar proportions of elements such as carbon, sulfur, nitrogen, and/or halogens that may adversely affect the properties of the resulting dielectric film.

Exemplary Doped Siloxane, Germoxane and/or Silagermoxane Compositions

In some embodiments, the present compositions further comprise one or more dopant compounds of the formula $D_aR^1_b$, where D is Sb, As, P, or Al; a is from 1 to 20; b is from 0 to 26 or an integer corresponding to the number of binding sites available on the a instances of D; each of the b instances of $R^1$ is independently H, alkyl, aryl, aralkyl, a halogen, O, $OR^2$, $NR^2_2$ or $AR^{2'}_3$; where $R^2$ is hydrogen, alkyl, aryl, aralkyl, or a halogen; $R^{2'}$ is hydrogen, alkyl, aryl, aralkyl or $A_yH_{2y+1}$; and y is an integer of from 1 to 4.

Doped siloxanes and/or added dopant compound(s) may be present in a doped siloxane composition in an amount to effect a desired dopant atom concentration (e.g., atom percent, mol percent) in a doped dielectric film. The amount of added dopant or of doped siloxane may be selected in terms of wt %, mol %, or on the basis of dopant at % relative to silicon and/or germanium atoms in a doped siloxane (and each of at %, mol % and wt % may easily be converted to the others by simple calculations employing the atomic masses [as reported in the Periodic Table of the Elements] of the component atoms of interest [e.g., Si, Ge, O, P, B, Al, etc.] in the mixture). The amount of dopant compound(s) and/or doped siloxane in the composition may be, for example, from 0.0001 mol % or wt % to 50 mol % or wt % (e.g., 0.001 mol % or wt % to 30 mol % or wt %, 0.01 mol % or wt % to 10 mol % or wt %, or any value or range of values therein).

The doped siloxane composition comprises one or more solvents suitable for undoped siloxane compositions as described herein. Similarly, the doped siloxane composition may further comprise one or more conventional additives, such as a surface tension reducing agent, a surfactant, a binding agent, a thickening agent, a photosensitizer, etc suitable for undoped siloxane compositions as described herein. Preferably, however, the composition is free from components that may introduce undesired impurities into the dielectric film formed from the composition (e.g., carbon, nitrogen, alkali metals, etc.).

Undoped and/or doped siloxane compositions as described provide dielectric precursor inks that yield substantially carbon-free undoped and/or doped dielectric films, whereas conventional spin-on glass (SOG) formulations and/or conventional printable dopant compositions typically comprise one or more carbon-containing monomeric precursor(s). Accordingly, after decomposition of such a SOG formulation, the resultant dielectric film may contain significant amounts of carbon due to incorporation of some of the carbon from the monomer. Thus, undoped and/or doped siloxane compositions as described advantageously provide undoped and/or doped dielectric precursor inks that may be employed in forming substantially carbon-free undoped and/or doped dielectric films.

Exemplary Methods for Making a Dielectric Film

In a still further aspect, the present invention relates to a method for making a dielectric film including the steps of coating or printing a composition containing a siloxane, germoxane, or silagermoxane on a substrate, then converting the coated or printed composition to a dielectric film. In some embodiments, a siloxane, germoxane, or silagermoxane composition as described herein may be printed on a substrate to form layers and/or features in a semiconductor device.

For example, the present dielectric precursor ink compositions may be coated or printed onto a semiconductor layer or a semiconductor island to form a gate dielectric in a thin-film transistor. Alternatively, the present compositions may be coated or printed onto one or more active semiconductor devices to form an interlayer dielectric layer. In still another alternative, the present composition may be printed over individual and/or groups of features and/or structures to provide insulation and/or a dopant source for those individual and/or groups of features and/or structures, yet leaving other individual and/or groups of features and/or structures exposed. Accordingly, the present compositions may be employed to print essentially any feature that may comprise an undoped or dielectric film. The thickness of a coated or printed dielectric film may be selected for a particular application, and may be from 2 nm to 100 μm (e.g., 1 μm to 10 μm, or any value or other range of values therein).

In some embodiments, the present compositions may be printed in a two-dimensional, ordered or non-ordered array of lines having a width of from 100 nm to 100 μm (e.g., 0.5 μm to 50 μm, 1 μm to 20 μm, or any other value or range of values therein). The lines may have an inter-line spacing of from 100 nm to 100 μm (e.g., 200 nm to 50 μm, 500 nm to 10 μm, or any other value or range of values therein). In addition, at least a subset of the lines may have a length of from 1 μm to 5000 μm (e.g., 2 μm to 2000 μm, 5 μm to 1000 μm, or any other value or range of values therein), and a thickness of from 0.001 μm to 1000 μm (e.g., 0.01 μm to 500 μm, 0.05 μm to 250 μm, or any other value or range of values therein). Furthermore, the lines may comprise a first set of parallel lines along a first axis, and a second set of parallel lines along a second axis perpendicular to the first axis. Although parallel and perpendicular lines may minimize adverse effects from adjacent lines and/or maximize the predictability of electromagnetic field effects from adjacent lines, the patterned lines may take any shape and/or take any course that can be designed and formed (e.g., by printing). Preferably, the composition is printed in such parallel or perpendicular lines to minimize dimensional variations amongst the printed lines, and to prevent uneven flow of the printed ink.

After printing or coating, the composition may then be converted to a dielectric film by heating. In general, forming the dielectric film comprises heating the coated or printed composition at a first, relatively low temperature in a soft-cure step, to remove solvent from the composition. The temperature may be less than or equal to about 200° C., and may be conducted for a length of time sufficient to remove substantially all solvent in the composition, typically from 10 sec to 12 hours, 1 min to 4 hours, 2 min to 1 hour, or any value therein. Forming the dielectric film may further comprise hard curing step, typically after substantially all solvent has been removed from the composition in a soft curing step. However, in some embodiments, forming the film may comprise a single curing step. A hard curing step generally comprises heating the printed or coated composition at a temperature of from about 100° C. to about 600° C., to form the dielectric film. Hard curing may be conducted for a length of time sufficient to form the dielectric film, typically from 1 min to 24 hours, 30 min to 12 hours, or any other value or range of values therein.

In certain embodiments where the siloxane composition further comprises a dopant (either intrinsic to a doped siloxane, or in the form of added dopant compound), the doped siloxane composition may be printed over semiconductor features to form a doped dielectric film, which may serve as a dopant source for an underlying semiconductor layer during a subsequent dopant diffusion or drive-in step. For example, after coating and/or printing a doped siloxane composition and forming a doped dielectric layer over semiconductor features to be doped, dopant drive-in and activation may be conducted (generally by annealing), typically at a temperature in the range of 750-1100° C. using, e.g., furnace annealing or Rapid Thermal Activation. Alternatively, the dopant may be driven into a semiconductor feature by UV-lamp flash annealing or laser irradiation, using a wavelength of light and/or a light power sufficient to diffuse a dopant from the dielectric into the semiconductor and/or activate the dopant once in the semiconductor.

In some embodiments, doped or undoped siloxane compositions are printed using inkjetting. Alternatively, other printing or deposition technologies besides inkjetting, such as flexographic, offset lithographic, gravure, screen and stencil printing, spin, slit, pen and/or extrusion coating, etc., may be utilized. Furthermore, siloxane compositions comprising different and/or complementary dopants may be employed in forming semiconductor devices and/or features. Simultaneous or sequential printing of complementary dopant materials may allow doping of semiconductor layers and/or features via a coating and/or printing process to substitute for relatively expensive masking layers, and eliminating other processing steps associated with photolithography.

The surface of one or more materials on which the undoped or doped siloxane composition is to be printed may be modified to improve wetting, optimize adhesion, flow rates, etc., and the ink formulation characteristics (e.g., viscosity) may be optimized to improve conformality over a semiconductor device feature. In still other embodiments, a dielectric film containing a dopant can be removed after drive-in/annealing (e.g., by etching). Etching of the film may be accomplished by exposure to one or more suitable etchants including, but not limited to, HF-based wet etchants (e.g., buffered oxide etch [BOE], native oxide etch [NOE], aq. pyridine:HF, etc.), HF-based or -producing vapors or gases, plasma etching, etc.

CONCLUSION/SUMMARY

Thus, in one aspect, the present invention provides doped and undoped siloxanes, germoxanes, and silagermoxanes that are substantially free from carbon and other undesired contaminants. In a second aspect, the present invention provides methods for making such doped and undoped siloxanes, germoxanes, and silagermoxanes. In still another aspect, the present invention provides compositions comprising doped and undoped siloxanes, germoxanes, and silagermoxanes and a solvent. In another aspect, the present invention provides a method for making doped and undoped dielectric films that are substantially free of carbon and other undesired contaminants.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method of making a siloxane, germoxane, or silagermoxane compound, comprising:
   a) mixing a linear, branched, cyclic or caged silane, germane, or silagermane containing at least three A atoms comprising units of the formula =(AH)—, -(AH$_2$)—, -(AH$_3$), -(c-A$_q$H$_{2q-1}$) and/or -(c-A$_q$H$_{2q-x}$)—, where each instance of A is independently Si or Ge, each instance of q is independently an integer from 3 to 12, and each instance of x is independently an integer from 0 to q, with a solvent; and
   b) reacting said silane, germane, or silagermane compound with an oxygen source selected from the group consisting of sulfur-based oxidants, alkali metal-based oxidants, alkaline earth metal-based oxidants, transition metal-based oxidants, lanthanide metal-based oxidants and/or actinide metal-based oxidants and that contains substantially no carbon atoms to form said siloxane, germoxane, or silagermoxane.

2. The method of claim 1, wherein said linear, branched, cyclic or caged silane, germane, or silagermane consists essentially of silicon and hydrogen.

3. The method of claim 1, wherein said linear, branched, cyclic or caged silane, germane, or silagermane further comprises one or more units of the formula of the formula DR$^1_p$, where each instance of D is independently Sb, As, P or B, each instance of p is independently an integer from 0 to 2, and each instance of R$^1$ is independently alkyl, aryl, aralkyl, H, or AR$^2_3$, where R$^2$ is H, or -A$_y$H$_{2y+1}$, and y is an integer from 1 to 4.

4. The method of claim 3, wherein D is P or B.

5. The method of claim 1, further comprising adding one or more dopant and/or dopant precursor compounds to said linear, branched, cyclic or caged silane, germane, or silagermane and said solvent prior to said reacting step to form a mixture.

6. The method of claim 5, wherein said one or more dopant and/or dopant precursor compounds are present in an amount providing from 0.0001 at % to 20 at % of dopant atoms in the mixture.

7. A method of making a polysiloxane, comprising:
   a) mixing a linear, branched, cyclic or caged silane, germane, or silagermane containing at least three A atoms comprising units of the formula =(AH)—, -(AH$_2$)—, -(AH$_3$), -(c-A$_q$H$_{2q-1}$) and/or -(c-A$_q$H$_{2q-x}$)—, where each instance of A is independently Si or Ge, each instance of q is independently an integer from 3 to 12, and each instance of x is independently an integer from 2 to q, with a solvent; and
   b) adding one or more dopant and/or dopant precursor compounds to said linear, branched, cyclic or caged silane, germane, or silagermane and said solvent to form a mixture; and
   c) after said adding step, reacting said silane, germane, or silagermane with an oxygen source that contains substantially no carbon atoms to form said polysiloxane.

8. The method of claim 7, wherein the oxygen source is selected from the group consisting of sulfur-based oxidants, alkali metal-based oxidants, alkaline earth metal-based oxidants, transition metal-based oxidants, lanthanide metal-based oxidants and/or actinide metal-based oxidants.

9. The method of claim 7, wherein the oxygen source is selected from the group consisting of air, O$_2$, O$_3$ and H$_2$O$_2$.

10. The method of claim 7, wherein said linear, branched, cyclic or caged silane, germane, or silagermane consists essentially of silicon and hydrogen.

11. The method of claim 7, wherein said one or more dopant and/or dopant precursor compounds comprises a compound of the formula D$_a$R$^1_b$, where D is Sb, As, P or B or Al; a is from 1 to 20; b is an integer corresponding to the number of binding sites available on the a instances of D; each of the b instances of R$^1$ is independently H, alkyl, aryl, aralkyl, a halogen, O, OR$^2$, NR$^2_2$ or AR$^{2'}_3$; where R$^2$ is hydrogen, alkyl, aryl, aralkyl, F, Cl, Br, or I; R$^{2'}$ is hydrogen, alkyl, aryl, aralkyl or A$_y$H$_{2y+1}$; and y is an integer of from 1 to 4.

12. The method of claim 11, wherein said one or more dopant and/or dopant precursor compounds comprises one or more soluble organoboranes, (organo)azaboranes, organoborates, boron oxides, BX$_3$, an adduct and/or salt of BF$_3$, white or red phosphorous, a phosphorous oxide, an organophosphines, an organophosphine oxide, an organophosphite, an organophosphate, a meta- or polyphosphate, an organophosphazenes, an organooxophosphazene, PX$_3$, PX$_5$, POX$_3$, P(NR$_2$)$_3$, O=P(NR$_2$)$_3$, or P(=NR)X$_3$, where X is a halogen and R is alkyl or aryl.

13. The method of claim 7, wherein said one or more dopant and/or dopant precursor compounds are present in an amount providing from 0.0001 at % to 20 at % of dopant atoms in the mixture.

14. A method of making a polysiloxane, comprising:
   a) mixing a polysilane containing at least 15 silicon atoms consisting essentially of units of the formula =(SiH)—, —(SiH$_2$)—, —(SiH$_3$), -(c-Si$_q$H$_{2q-1}$)— and/or -(c-Si$_q$H$_{2q-x}$)—, where each instance of q is independently an integer from 3 to 12, and each instance of x is independently an integer from 2 to q, with a solvent; and
   b) reacting said polysilane with an oxygen source that contains substantially no carbon atoms to form said polysiloxane.

15. The method of claim 14, wherein the oxygen source is selected from the group consisting of sulfur-based oxidants, alkali metal-based oxidants, alkaline earth metal-based oxidants, transition metal-based oxidants, lanthanide metal-based oxidants and/or actinide metal-based oxidants.

16. The method of claim 14, wherein the oxygen source is selected from the group consisting of air, O$_2$, O$_3$ and H$_2$O$_2$.

17. The method of claim 14, wherein said linear, branched, cyclic or caged silane, germane, or silagermane further comprises one or more units of the formula of the formula DR$^1_p$, where each instance of D is independently Sb, As, P or B, each instance of p is independently an integer from 0 to 2, and each instance of R$^1$ is independently alkyl, aryl, aralkyl, H, or AR$^2_3$, where R$^2$ is H, or -A$_y$H$_{2y+1}$, and y is an integer from 1 to 4.

18. The method of claim 14, further comprising adding one or more dopant and/or dopant precursor compounds to said linear, branched, cyclic or caged silane, germane, or silagermane and said solvent prior to said reacting step.

19. The method of claim 18, wherein said one or more dopant and/or dopant precursor compounds comprises a compound of the formula D$_a$R$^1_b$, where D is Sb, As, P or B or Al; a is from 1 to 20; b is an integer corresponding to the number of binding sites available on the a instances of D; each of the b instances of R$^1$ is independently H, alkyl, aryl, aralkyl, a halogen, O, OR$^2$, NR$^2_2$ or AR$^{2'}_3$; where R$^2$ is hydrogen, alkyl, aryl, aralkyl, F, Cl, Br, or I; R$^{2'}$ is hydrogen, alkyl, aryl, aralkyl or A$_y$H$_{2y+1}$; and y is an integer of from 1 to 4.

20. The method of claim 18, wherein said one or more dopant and/or dopant precursor compounds are present in an amount providing from 0.0001 at % to 20 at % of dopant atoms in the mixture.

* * * * *